United States Patent
Ho et al.

(10) Patent No.: US 11,262,183 B2
(45) Date of Patent: Mar. 1, 2022

(54) OPTICAL INTERFERENCE IMAGING DEVICE AND ITS APPLICATION

(71) Applicant: Apollo Medical Optics, Ltd., Taipei (TW)

(72) Inventors: Tuan-Shu Ho, Taipei (TW); I-Ling Chen, Taipei (TW); Dan Ji, Taipei (TW); Sung Wei Lu, Taipei (TW); Tzu Wei Liu, Taipei (TW); Jen Yu Tseng, Taipei (TW); Ting Yueh Lin, Taipei (TW); Chih Wei Lu, Taipei (TW); Jia-Wei Lin, Taipei (TW); Yo Cheng Chuang, Taipei (TW); Sheng-Lung Huang, Taipei (TW)

(73) Assignee: Apollo Medical Optics, Ltd., Taipei (TW)

( * ) Notice: Subject to any disclaimer, the term of this patent is extended or adjusted under 35 U.S.C. 154(b) by 96 days.

(21) Appl. No.: 16/648,226

(22) PCT Filed: Sep. 18, 2018

(86) PCT No.: PCT/US2018/051609
§ 371 (c)(1),
(2) Date: Mar. 17, 2020

(87) PCT Pub. No.: WO2019/056022
PCT Pub. Date: Mar. 21, 2019

(65) Prior Publication Data
US 2020/0271436 A1    Aug. 27, 2020

Related U.S. Application Data

(60) Provisional application No. 62/560,131, filed on Sep. 18, 2017, provisional application No. 62/560,090, filed on Sep. 18, 2017.

(51) Int. Cl.
G01B 9/02      (2006.01)
G01B 9/02091   (2022.01)
(Continued)

(52) U.S. Cl.
CPC .......... G01B 9/02091 (2013.01); A61B 3/102 (2013.01); A61B 5/0066 (2013.01); G01B 9/02025 (2013.01); G01B 9/02037 (2013.01)

(58) Field of Classification Search
CPC ............ G01B 9/02091; G01B 9/02025; G01B 9/02037; G01B 9/02057; A61B 3/102; A61B 5/0066; A61B 3/107; A61B 5/444
See application file for complete search history.

(56) References Cited

U.S. PATENT DOCUMENTS 6,307,636 B1    10/2001  Spink
2007/0238955 A1*  10/2007  Tearney ............. A61B 1/00167
                                                600/407
(Continued)

FOREIGN PATENT DOCUMENTS

WO    WO 2016/126861 A1    8/2016
WO    WO 2017/046225 A1    3/2017

OTHER PUBLICATIONS

Takashi Endo, Profilometry with line-field Fourier-domain interferometry, Feb. 2005, vol. 13, No. 3, pp. 695-701 (Year: 2005).*
(Continued)

Primary Examiner — Michael P LaPage
(74) Attorney, Agent, or Firm — Chung-Hsing Liang

(57) ABSTRACT

Provided herein are devices and systems comprising an illumination module configured to provide a source light to an optical interference module, which converts the source light to a line of light and processes light signal; an interference objective module, which handles light from the optical interference module and processes light signal gen-
(Continued)

erated from a sample; a two-dimensional camera configured to receive a backscattered interference signal from the sample, and a data processing module which processes the interference signal into an image.

29 Claims, 11 Drawing Sheets

(51) Int. Cl.
    *A61B 3/10* (2006.01)
    *A61B 5/00* (2006.01)
    *G01B 9/02015* (2022.01)

(56) References Cited

U.S. PATENT DOCUMENTS

| | | | | |
|---|---|---|---|---|
| 2007/0291277 | A1* | 12/2007 | Everett | G01N 21/4795 356/497 |
| 2011/0043661 | A1* | 2/2011 | Podoleanu | H04N 5/33 348/239 |
| 2013/0068967 | A1 | 3/2013 | Kleppe et al. | |
| 2014/0028974 | A1* | 1/2014 | Tumlinson | G01B 9/02043 351/206 |
| 2015/0077760 | A1* | 3/2015 | Koerner | G01B 9/02008 356/496 |
| 2016/0320598 | A1* | 11/2016 | Dubois | G02B 21/33 |
| 2017/0231488 | A1 | 8/2017 | Tumlinson et al. | |
| 2017/0363415 | A1* | 12/2017 | Frisken | G01B 9/02032 |

OTHER PUBLICATIONS

Watanabe et al.,"Three-dimensional imaging by ultrahigh-speed axial-lateral parallel time domain optical coherence tomography", Optics Express, US, vol. 14, No. 12 (Jun. 1, 2006).

* cited by examiner

FIG. 1A/B
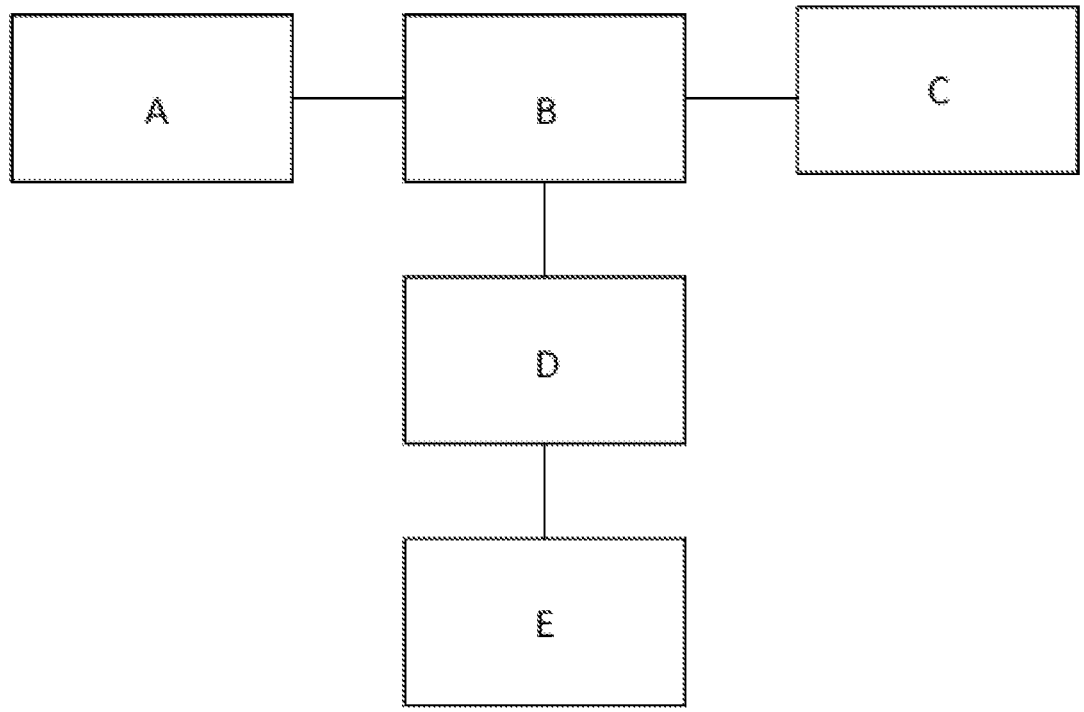
1A
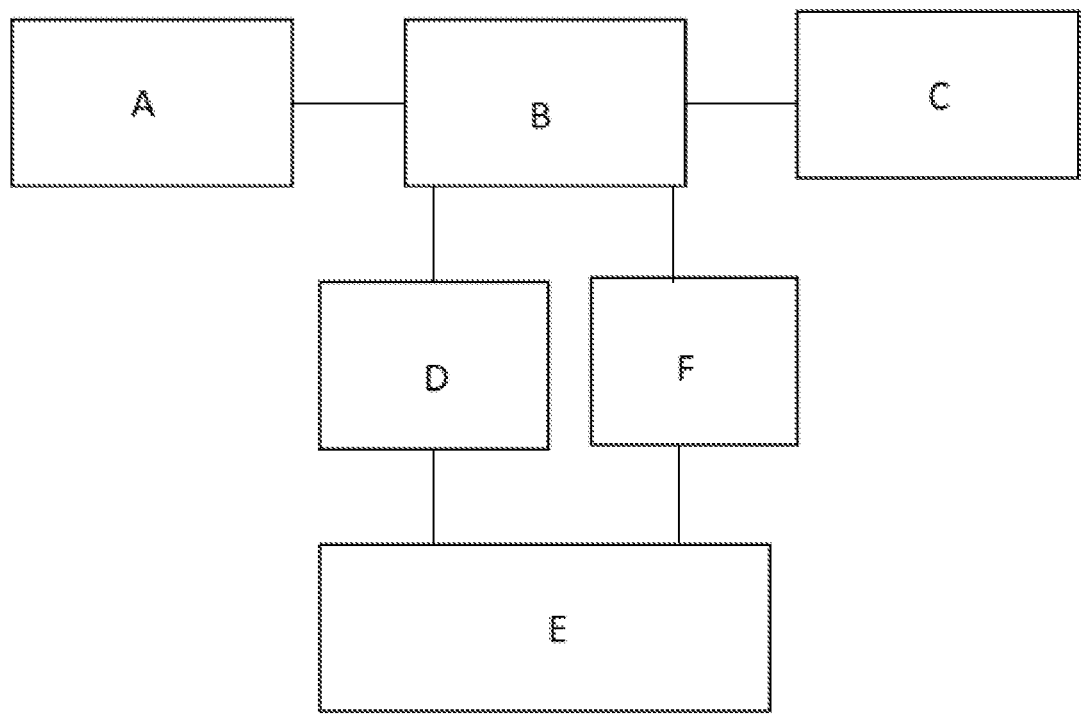
1B

FIG. 2A/B
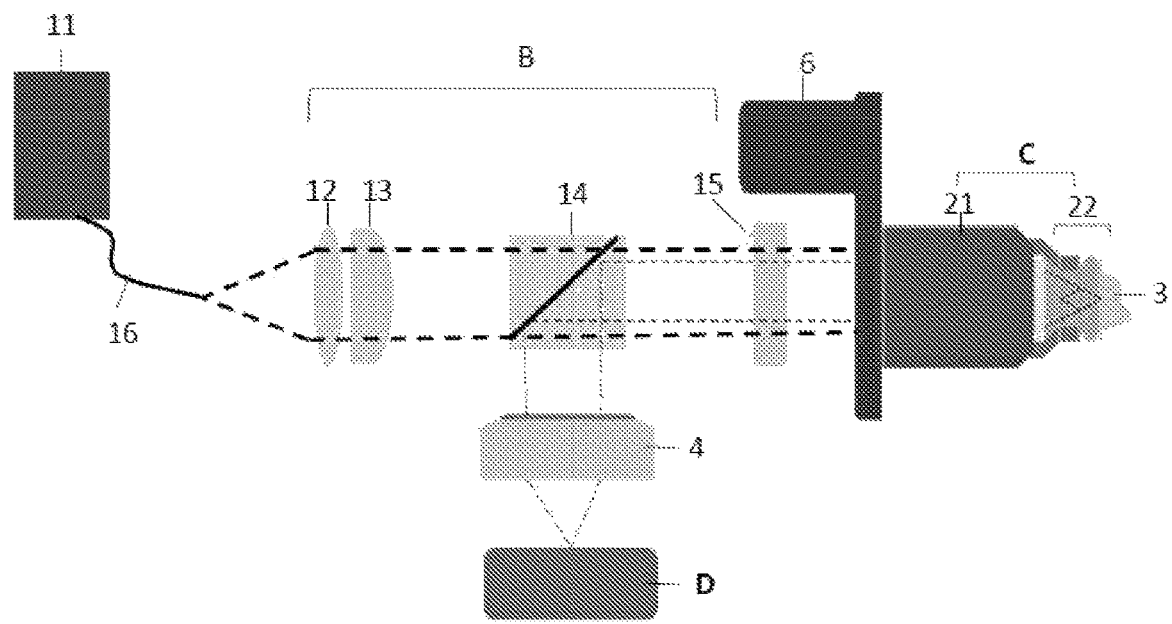
2A
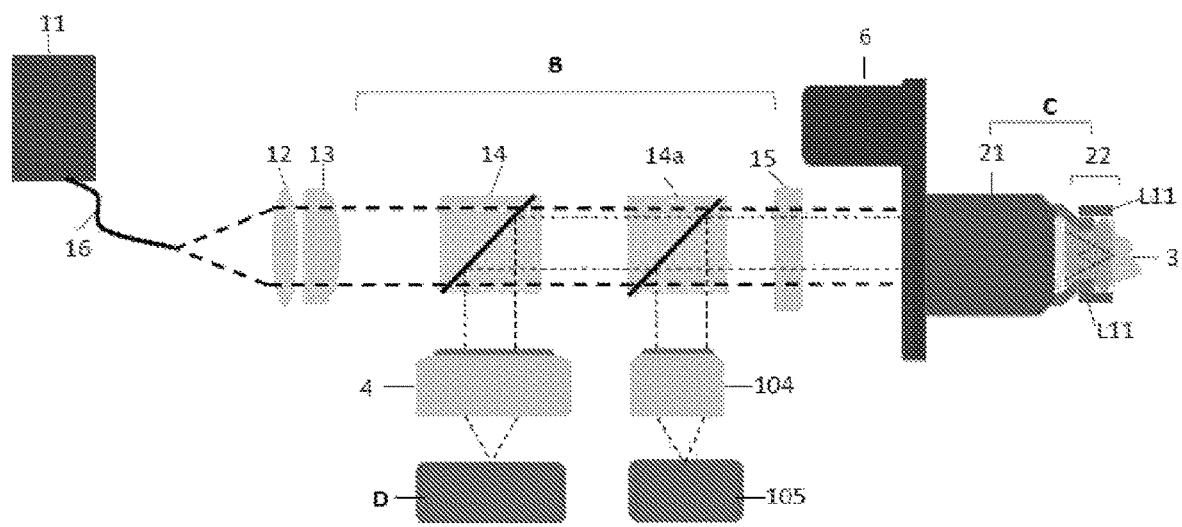
2B

FIG. 3
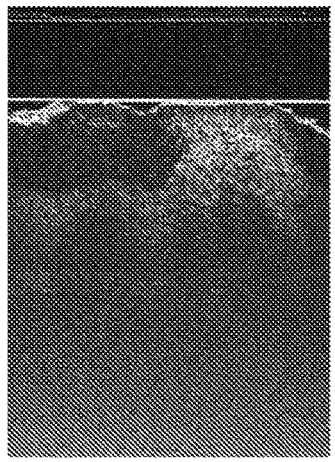
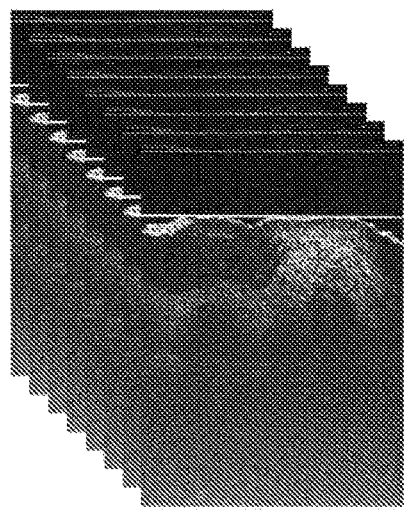
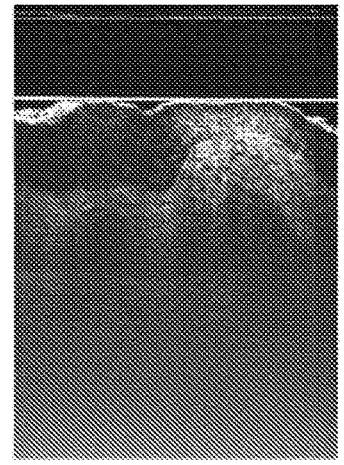
3A  3B  3C

FIG. 4A/4B
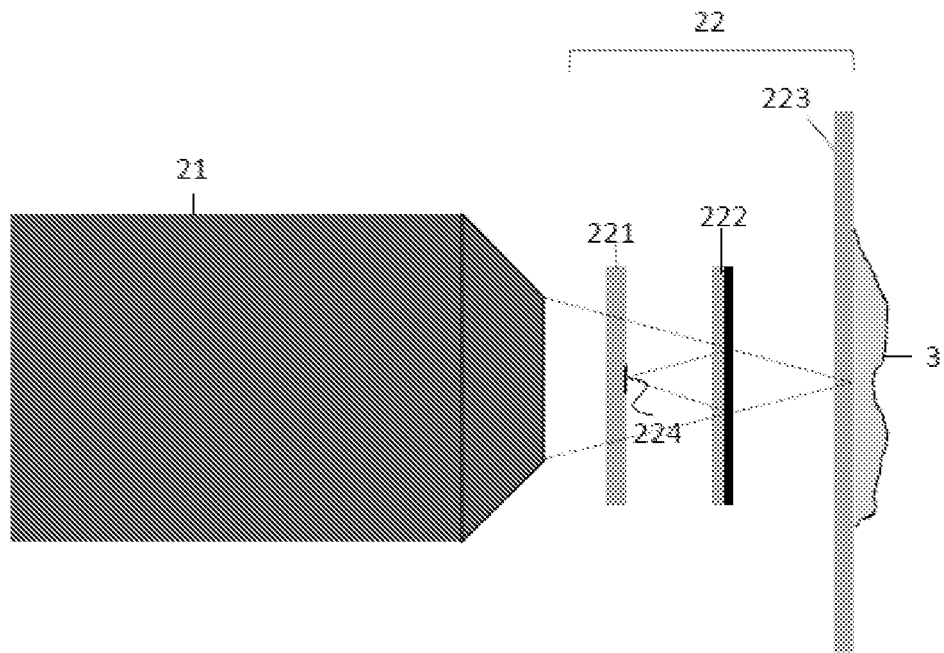
4A
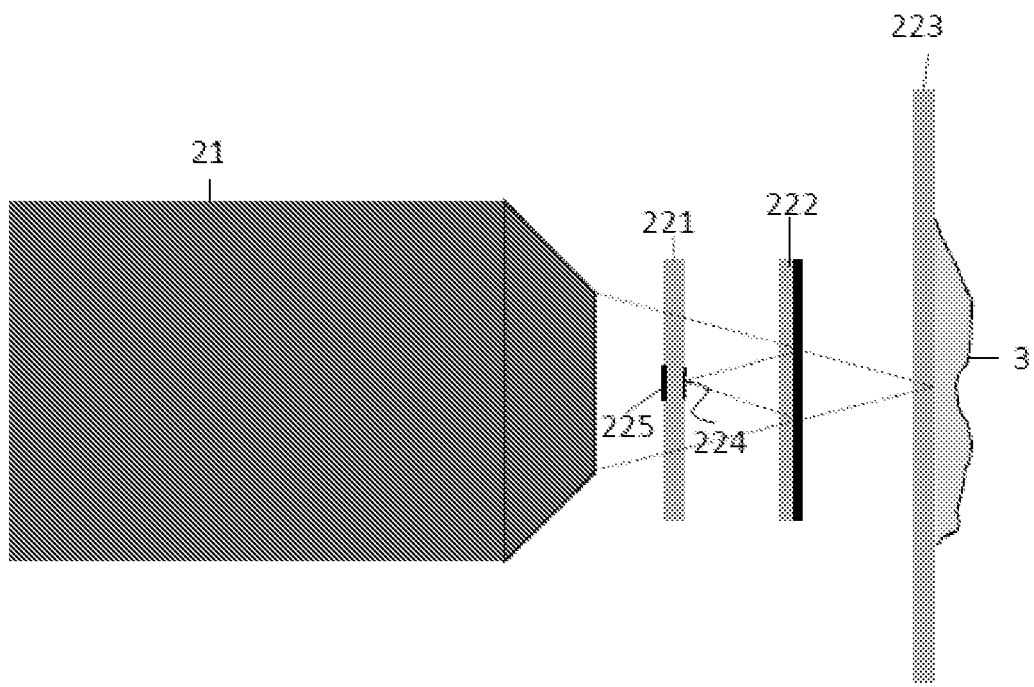
4B

FIG. 10A-C
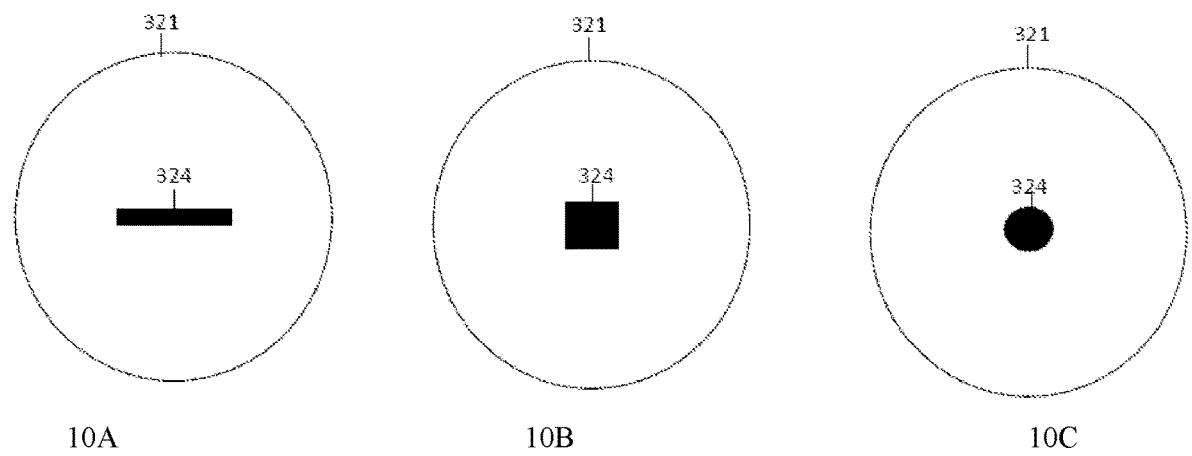
10A 10B 10C

OPTICAL INTERFERENCE IMAGING DEVICE AND ITS APPLICATION

BACKGROUND OF THE INVENTION

According to the statistic of World Health Organization, skin cancer has grown year-on-year in the past decade globally, closely related to lifestyle, aging society, and the destruction of the global ozone layer.

Skin cancers are cancers that arise from the skin. They are due to the development of abnormal cells that have the ability to invade or spread to other parts of the body.

Optical Coherence Tomography (OCT) is a technique for performing noninvasive high resolution cross-sectional imaging that can provide images of tissue structure (e.g., skin tissues) on the micron scale.

SUMMARY OF THE INVENTION

The present invention provides an invention device/system (i.e., an interference imaging device/system), especially to a line scan interference imaging device having a two-dimensional camera to receive the interference signal and achieve good quality of images and image resolution. The device comprises a line shaped reflective mirror on the interference objective module, thereby increasing the efficiency of utilizing light.

In some aspect provides a device/system comprising an illumination module configured to provide a source light to an optical interference module, which converts the source light to a line of light and processes light signal; an interference objective module, which handles light from the optical interference module and processes light signal generated from a sample; a two-dimensional camera configured to receive a backscattered interference signal from the sample, and a data processing module which processes the interference signal into an image.

In another aspect provides a device/system comprising an illumination module configured to provide a source light (such as a line of light, or an area of light) to an optical interference module; an interference objective module comprising an objective and an interference means, which handles light from the optical interference module and process light signal generated from a sample; a two-dimensional camera to receive a backscattered interference signal from the sample; and a data processing module for analyzing light signals and providing a sample imaging, wherein device/system is configured to make the objective to accept incident light in an arrangement having a focal spot of the incident light between a focal plane and a principal plane of the objective.

In yet another aspect provides a method for imaging a sample comprising imaging test light in depth emerging from a sample, and imaging a contrast image of absorption, dispersion, and/or scattering from a substructure of the sample to provide a dynamic state of the sample, by a device or a system described herein.

In yet another aspect provides a method for imaging a sample comprising making an objective in the invention interference objective module which handles light from the optical interference module and process light signal generated from a sample to accept incident light in an arrangement having a focal spot of the incident light between a focal plane and a principal plane of the objective from an illumination module, and processing an interference signal generated said interference module into an image by a data processing module.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which:

FIG. 1A/B illustrate the block diagrams exemplifying the invention device/system comprising an illumination module A, an optical interference module B, an interference objective module C next to an area of samples, a two-dimensional camera D, and an image processing module E (1A). The invention device/system is optionally included an imaging guiding module comprising another two-dimensional camera F (1B).

FIG. 2A/B illustrates an exemplary invention device/system without incorporating a second two-dimensional (2D) camera (2A) and with a 2D camera (2B).

FIG. 3A-C show the exemplary images produced by an embodiment of the invention device/system. Image produced by a 1D-camera is shown in FIG. 3A. Image produced by a 2D-camera is shown in FIG. 3C. FIG. 3B shows superimposing several images to provide a low number of speckles in images.

FIG. 4A/B illustrate the designs of the exemplary interference objective module without a black spot (4A) or with a black spot (4B).

FIG. 10A-C illustrate examples of the reflective reference mirror with different shapes.

DETAILED DESCRIPTION OF THE INVENTION

Figure 5:
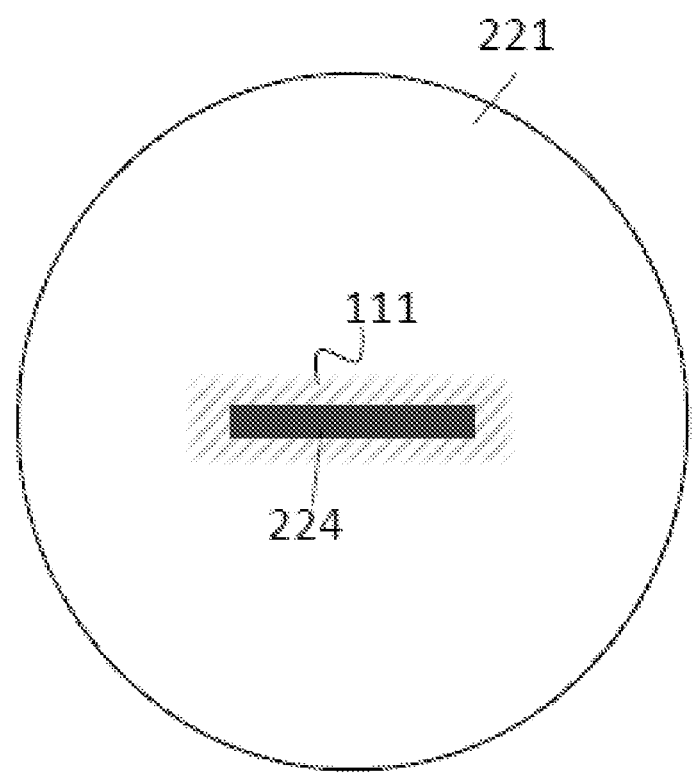
FIG. 5 illustrates an embodiment of the first glass having a line shaped reflective mirror.

In recent years, optical coherence tomography (OCT) has been widely applied on three-dimensional (3-D) image reconstruction of skin tissue, or cornea. It is known that in epidermis, to non-invasively probe the layer parameters (LPs), such as average total thickness (a-TT), average number of layers (a-NOLs), and average cellular layer thickness (a-CLT), for stratum corneum (SC) becomes important for evaluating the skin moisturization of epidermis. However, to apply OCT technology to skin tissue imaging, axial resolution better than 1.2 µm in tissue is the doorsill to measure LPs of the SC. Besides, the morphology of single 3-D epidermal cell is also important for early detection of normal and abnormal cells of pre-cancer diagnosis. These all require sub-micron spatial resolution in tissue.

Provided herein are devices and systems that apply OCT technology (e.g., a FF-OCT) to skin tissue or cornea imaging applying a line light illuminated on a sample which produces a cross-sectional scanning image with unexpectedly clear and low speckles image quality, with a two-dimensional camera. Particularly, the present invention provides devices and systems having a line shaped reflective mirror parallel the line shaped light on an interference objective module to be detected by a two-dimensional camera, so as to achieve the efficiency of light utilization and improve the image scanning speed.

In some embodiments, there are provided a device/system comprising an illumination module configured to provide a source light (such as a line of light, or an area of light) to an optical interference module; an interference objective module, which handles light from the optical interference module and process light signal generated from a sample; a two-dimensional camera to receive a backscattered interference signal from the sample; and a data processing module for analyzing light signals and providing a sample imaging.

There are provides an embodiment of the invention device/system as shown FIG. 1A, which comprises an illumination module A configured to provide a source light (e.g., a line of light, or an area of light) to an optical interference module B, an interference objective module C which processes and projects the light to the interference objective module B therefrom, and direct the line of light on a sample 3; a two-dimensional camera D configured to receive a backscattered interference signal from the sample 3; and a data processing module E, which processes the interference signal into an image.

In some embodiments, the illumination module (such as a light source 11) comprises a spontaneous emission light source, an amplified spontaneous emission light source, a superluminescent diode, a light emitting diode (LED), a broadband supercontinuum light source, a mode-locked laser, a tunable laser, a Fourier-domain mode-locked light source, an optical parametric oscillator (OPO), a halogen lamp, or a doped crystal fiber such as a $Ce^{3+}$:YAG crystal fiber, a $Ti^{3+}$:$Al_2O_3$ crystal fiber, a $Cr^{4+}$:YAG crystal fiber, or the like. In certain embodiments, the light source module comprises a $Ce^{3+}$:YAG crystal fiber, $Ti^{3+}$:$Al_2O_3$ crystal fiber, or a $Cr^{4+}$:YAG crystal fiber. In certain embodiments, the illumination module comprises a $Ti^{3+}$:$Al_2O_3$ crystal fiber. For example, the light source module is $Ti^{3+}$:$Al_2O_3$ crystal fiber light source with power of 0.5 mW to 500 mW, or 4 to 100 mW, or 10 to 50 mW, or 20 to 40 mW, or other suitable power range.

In some embodiments, the optical interference module is configured to generate a line pattern light projected by a light source in the illumination module. In certain embodiments, the optical interference module comprises an anamorphic lens such as a cylindrical lens, or a round-to-linear fiber bundle, a diffractive optical element, a special-designed optical diffuser, or the like. A skilled person in the art would readily adapt other suitable means to produce line shaped light with various the aspect ratio such as 3 to 100, or 5 to 20, or other suitable ratios. Other suitable optical components known in the art to produce a thin light can be used without limitations.

In some embodiments, the interference objective module comprises an objective and an interference means configured to process the source light such as a line of light projected by an optical interference module, to a sample and receive a backscattered signal therefrom to generate an interference signal. In some embodiments, the interference objective module is a Mirau-type interference objective module, a Michelson-type interference module, a Mach-Zehnder interference objective module, or any suitable interference type objective module readily recognized by a skilled person in the art.

In some embodiments, the objective is a Mirau-type interference objective module comprising an immersed objective having the immersed solution with a refractive index approaching to the refractive index of the sample. For example, if the sample is a skin, the refractive index will be in a range of about 1.2 to about 1.8, preferably about 1.3 to about 1.5. In some embodiments, the media comprises water, silicone oil, ethanol, glycerol, pyrex, ultra sound gel, or combinations thereof. In certain embodiments, the media comprises water, silicone oil, or glycerol. In certain embodiments, the media comprises water.

In some embodiments, as shown in FIG. 1B, the invention device/system further comprises an imaging guiding module F comprising a camera lens and a second 2D-camera used for imaging guiding. The imaging guiding module provides a large area image of the sample (e.g., a detailed large area of sample surface). The imaging guiding module and the interference objective module share the same optical channel or path and thus provide overlapped field of views as illustrated in FIG. 2B.

FIG. 2A provides an exemplary invention system/device. A light is generated by an illumination module comprising an exemplary light source 11 and transport to collimation lens 12 via an optical fiber 16. The light is transformed to a line shaped light by, for example, a cylindrical lens 13 and then passes through polarization beam splitter 14 and quarter wave plate 15 to convert the line shaped light with circular polarization. The light then enters an interference objective module C. In some embodiments, the interference objective module C comprises an objective 21 and an interference means 22. When the light (such as a line-shaped light) projects to sample 3 through interference objective module C, the backscattered light by sample 3 passes through interference objective module C to beam splitter 14 and provides light signal to a two-dimensional camera D via a projection lens 4. The signals are then further processed by a data processing module (not shown) to provide sample imaging. It is known in the art that a line scan light is processed by a one-dimensional camera since there is no need to record an area other than a one dimensional "line". It is surprisingly found that by utilizing a 2-D camera D with a special design, a high image signal to noise ratio, high resolution cress-sectional image is produced in comparison with the use of a 1-D camera. It is designed to utilize a z-axial piezoelectric transducer (PZT) 6 to scan interference objective module C in the Z direction. The line-shaped light with the interference signal will project onto the two-dimensional camera D with part of the pixel in a narrow rectangular area via a projection lens 4. After recording the PZT scanned interference signal, each column in the narrow rectangular area is processed by a data processing module E to produce cross-sectional images. Thus, a scan can produce several cross-sectional images. After superimposing the several cross-sectional images, a high image signal to noise ratio, high resolution cross-sectional image is produced.

In some embodiment, the interference means comprises horizontally arranged glasses including a first glass plate, a second glass plate and a third glass plate. The first glass plate comprises the reflective mirror configured to have a shape parallel the line of light. The second glass plate is configured to have the light transmitted partially to the third glass plate. For instance, the reflective mirror can be formed on the first glass plate having a shape of thin line with aspect ratio of about 1 to 5000, especially 4 to 1000, especially 8 to 250, especially 10 to 100, an artisan can adjust the ratio in need. The range of the aspect ratio of the reflective mirror can determine the range of field of view (FOV). In some embodiments, the second glass plate can be used as a beam splitter having a refractive ratio of about 5% to 30%, preferably 5% to 20% to avoid the stray light reflected by the glass-sample interface. Furthermore, those three glass plates have a refractive index matching the sample's refractive index, for example in a range of about 1.2 to about 1.8, preferably about 1.3 to about 1.5, so as to avoid the stray light produced by the glass-sample interface.

It is found by utilizing a 2-D camera D instead of a 1-D camera typically associated with line-shaped light related optical module known in the art for scanning sample to acquire a cross-sectional image, an unexpected superior result with high image clarity and quality was achieved where such design effectively boost image signal to noise ratio and reduce number of image speckles. As evidenced by the sample images in FIG. 3, obvious speckles are found in FIG. 3A image which was acquired by a 1D camera. The image is blurry with poor quality. On the other hand, compared with the image from FIG. 3A, the image of FIG. 3C, which was produced by a 2D camera, appears to have clear image signal with much less number of speckles. The reason that the use of a 2D camera in such design associated with a line of light has better image quality compared with one from a 1D camera (which is the typical approach known in the art) is because 1D camera can only receive 1 pixel wide sample image while the 2D camera can receive more than 1 pixel image data. By superimposing several images in accordance with the practice of the present invention as illustrated in FIG. 3B, a clear image with a low number of speckle was acquired. However, it is also found that if the stacking thickness is too thick, the image becomes blurry in certain characters of the image. Thus, it is found that the use of a 2D camera in such design only works under a range of thickness of image stacking. The optimum superposition thickness in some embodiments is 2 to 256 pixel, 4 to 128 pixel, or 4 to 64 pixel. In some embodiments, the optimum superposition thickness is 4 to 64 pixel. For example, 8 pixel is used to generate FIG. 3C. It is also surprisingly found that such 2-D camera design reduces the number of lenses needed making the module simpler due to the fact that the 2D camera can be flexibly adjusted for the measuring area allowing easy use of different aspect ratio of the optical designs. The reduced number of lenses significantly shortens the manufacturing time and effort to produce the invention device/system.

In some embodiments, the device/system further comprise an imaging guiding module comprising a projection lens 104 and a second 2D camera 105 for imaging guiding.

The device/system incorporates an imaging guiding module which provides a large (macro) image with skin surface detail. As shown in FIG. 2B, besides the 2D camera D associated with an exemplary Mirau type interference objective module, which provides a high-resolution optical imaging, an image guiding module comprising a camera lens 104 and a 2D-camera 105 is included in the device/system where the beam splitter 14a is used to direct the signals to 2D-camera 105. The two imaging systems share the same optical channel/path; therefore, the FOVs of them are overlapped and have a fixed relative position. A light source such as a LED (L11) cycling around the interference means 22 is incorporated to provide light for the imaging guiding module. The light source L11 has a different wavelength or time distribution from the illumination module, thus the signal produced by light source L11 by the sample are all collected by 2D-camera 105 to produce a large image of skin surface.

The FOV of the imaging guiding module is large than the FOVs of high-resolution imaging module (i.e., the interference objective module). While examining a sample (e.g., a lesion, or a cornea), the imaging guiding module is used to take a large image of the sample area first. Then, the interference objective module is attached onto the sample allowing the image guiding module to image the surface of the sample. An algorithm is used to calculate where the FOV of guiding image is on the first large image. Because the position between guiding image and high-resolution image is fixed, the position of high resolution image can be pinpointed on the large image.

An exemplary invention interference objective module and how it works is illustrated in FIGS. 4A, 4B and 5.

An exemplary interference means 22 is shown in FIG. 4A. In some embodiments, the interference means comprises a first glass plate 221 coated with a reflective mirror 224, a second glass plate 222, and a third glass plate 223 wherein the reflective mirror 224 is coated to generate a reference arm and produce interference with the returned scattered light by sample 3. As shown in FIG. 4A, the reflective mirror 224 coated on the first glass plate 222 is linear and parallel to focused line shaped light 111.

In other embodiments, as illustrated in FIG. 4B, a first glass plate 221 further comprises a black spot 225 on the opposite side of the first glass plate 221 at a position corresponding to the reflective mirror 224.

The transparent first glass plate 221, which is closest to the objective 21, is partially coated with a reflective mirror 224 so that the central region of the surface toward the focal plane is highly reflective, while and the central region of the surface toward the objective 21 has a black spot 225, which is absorptive to block the stray light. In some embodiments, the position of the black spot is on the same side of the reflective mirror 224, where the black spot covers the reflective reference mirror 224, so as to absorb the stray light from the first glass plate. The transparent third glass plate 223, which is (partially) contacted with the sample 3, is set to a (range of) position so that the focal plane of the objective lens is near the sample.

The second glass 222 is coated so that the surface toward the third glass plate 223 is partially reflective. This coated surface is served as the beam splitter in a Mirau type interferometer, and the position of the transparent second plate 222 is set to a position so that the highly reflective region 224 is on the focal plane of the objective lens.

As illustrated in FIG. 4A, the deviation within 20 degrees of angle is defined as parallel. In some embodiments, it is within 15 degrees of angle, within 10 degrees of angle, or within 5 degrees of angle. Furthermore, the reflective mirror 224 has an adjustable aspect ratio about 3 to 10, and preferably about 5 to 8. Accordingly, the architecture of such design of a coated line shaped reflective mirror on the first glass plate makes the full use of light. In some embodiments, the second glass plate 222 has a refractive ratio of about 5% to 30%, preferably 10% to 20%, or any other suitable ratio as needed based on the conditions. The third glass plate 223 is fully transparent for fitting with sample 3 allowing the line-shaped light to penetrate and illuminate sample 3.

In some embodiment, the interference means comprises horizontally arranged glasses including a first glass plate, a second glass plate and a third glass plate. The first glass plate comprises the reflective mirror configured to have a shape parallel the line of light. The second glass plate is configured to have the light transmitted partially to the third glass plate. For instance, the reflective mirror can be formed on the first glass plate having a shape of thin line with aspect ratio of about 1 to 5000, especially 4 to 1000, especially 8 to 250, especially 10 to 100, an artisan can adjust the ratio in need. The range of the aspect ratio of the reflective mirror can determine the range of field of view (FOV). In some embodiments, the second glass plate can be used as a beam splitter having a refractive ratio of about 5% to 30%, preferably 5% to 20%. Furthermore, those three glass plates have a refractive index matching the sample's refractive index, for example in a range of about 1.2 to about 1.8, preferably about 1.3 to about 1.5, so as to avoid the stray light produced by the glass-sample interface.

Figure 6A:
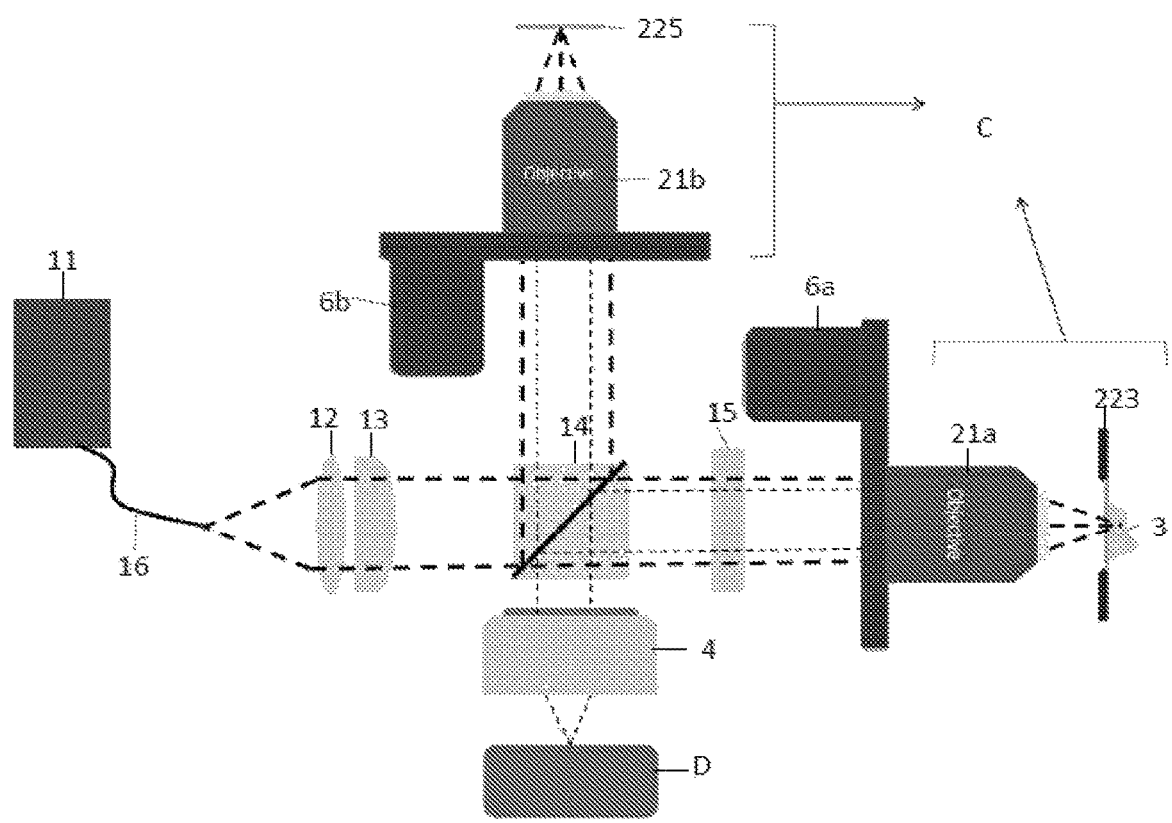
FIG. 6A/B illustrates yet another embodiment of the invention device/system, where a Michelson type objective is used without an imaging guiding module (6A) or with an imaging guiding module (6B).
Figure 6B:
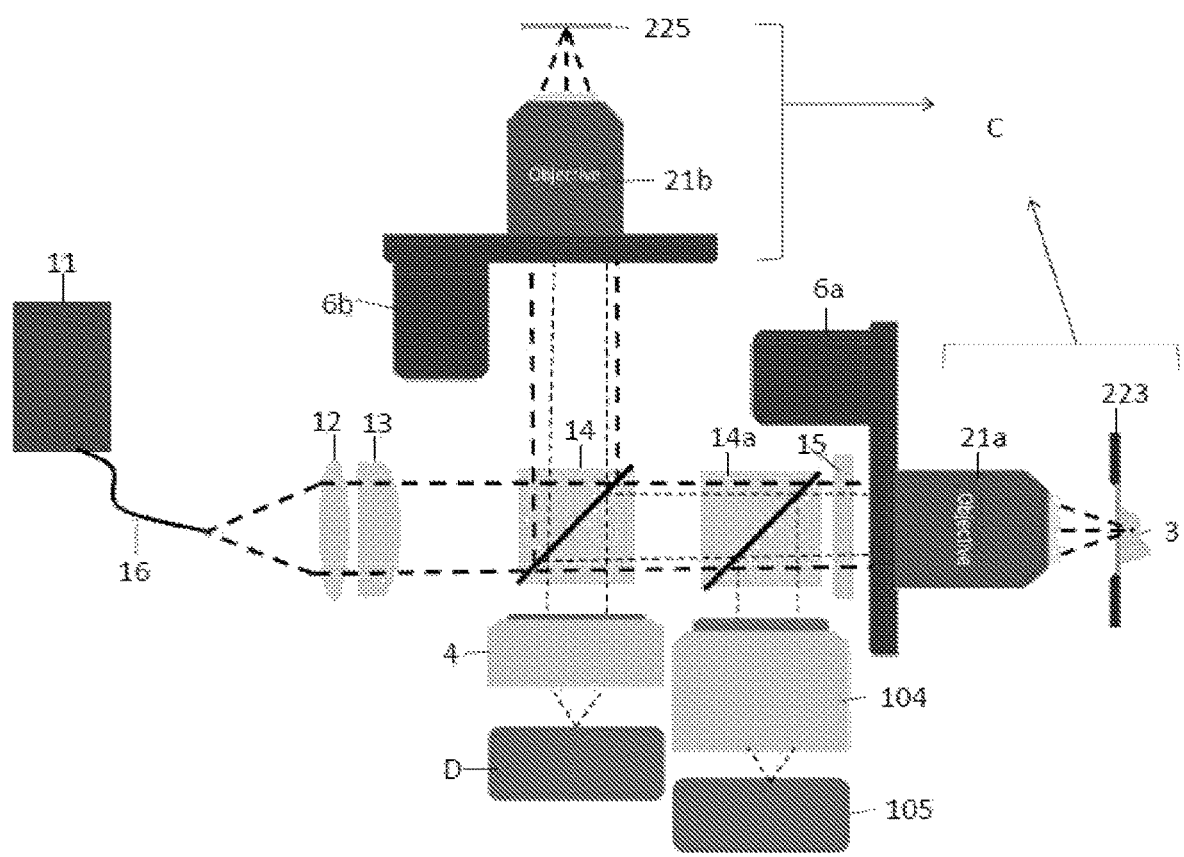

FIG. 6A/6B provides yet another embodiment where a Michelson-type interference objective module is used in the invention device/system. In some embodiments, the invention device/system is a Michelson-type interference imaging device/system, comprising the same illumination module and optical interference module, and optional imaging guiding module as in FIG. 2A/2B, except the use of a different interference objective module C. The interference objective module C comprises an objective 21a and a third glass plate 223 attached to a sample 3 thereon to produce a sample arm, and an objective 21b and a reflective mirror 225 to produce a reference arm. When the line light illuminated on the sample 3 and the reflective mirror 225 simultaneously and reflected therefrom, the interference signal will be created and collected by a two-dimensional camera D via a projection lens 4, then produces a cross-sectional image by a data processing module, while the imaging guiding module comprising a projection lens 104 and a 2D camera 105 to provide a large sample image for correlation of the cross-sectional image.

In some embodiments, the optical interference module further comprises a switch configured to toggle the light output between the line of light and an area of light, thereto switching between line-scan mode and full-field mode for the device allowing the user to acquire cross-sectional images and/or en-face images (e.g., to acquire a 3-D slice data) of a sample. Such design allows users to acquire the whole sample information.

Figure 7:
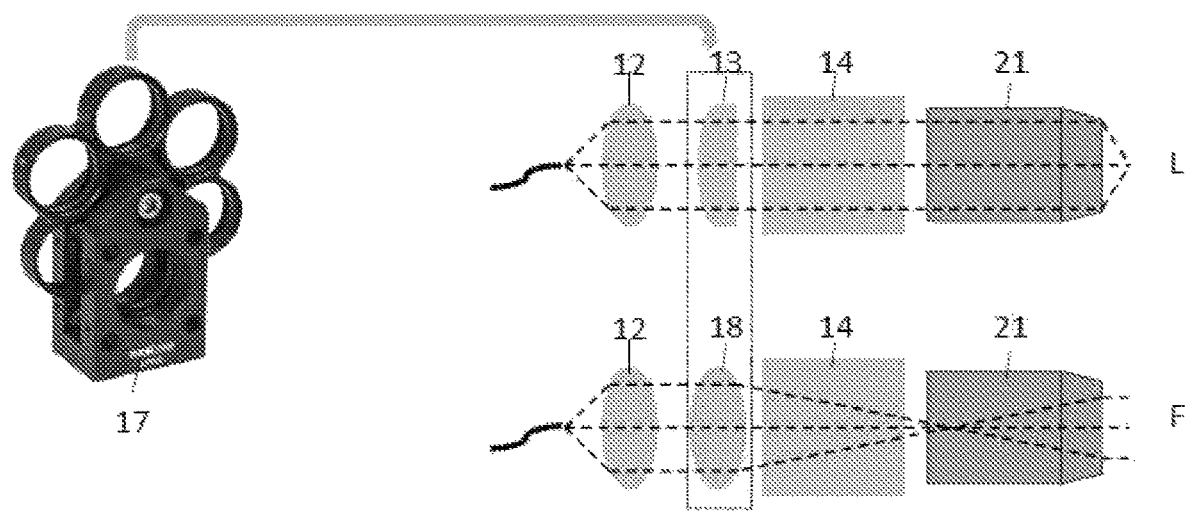
FIG. 7 provides yet another embodiment of an exemplary design of the invention device/system having a switch to change the illumination mode.

In order to acquire more structure information from a sample, in some embodiments, the optical interference module further comprises a switch 17 configured to provide different lighting mode as shown in FIG. 7. In some embodiments, there are two modes included to be changed; one is line light illuminating mode L, another is area light illuminating mode F, in which the switch 17 (e.g., Thorlabs CFW6) is disposed between the collimation lens 12 and the polarization beam splitter 14 to toggle the cylindrical lens 13 and the achromatic lens 18 fitted in the lens holders of switch 17, so as the illumination mode is switched to line light illumination mode L for acquiring cross-sectional images, or to area light illumination mode F for acquiring en-face images, which can lead to three-dimensional volumetric images. In some embodiments, such toggle switch design is not limited to the changes of line light illuminating mode and area illuminating mode; all other suitable modes with different lens may be used in accordance with the practice of the invention.

In some embodiments, the invention device/system is configured to make the stray light be focused on the edge and outside imaging range of the 2D camera D.

Figure 8:
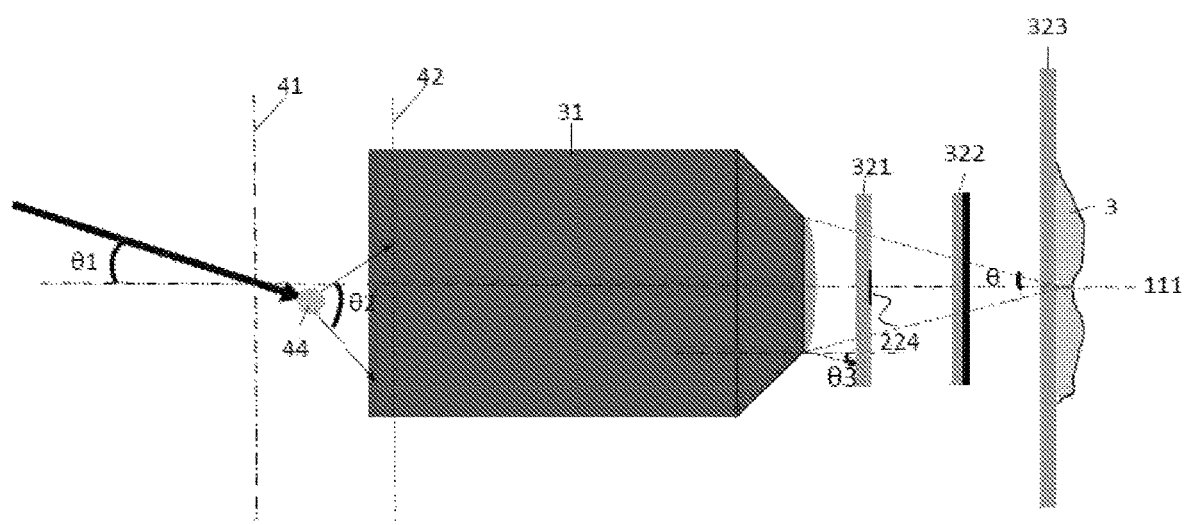
FIG. 8 illustrates an exemplary invention device/system comprising an interference objective module wherein the objective 31 is configured to make the focal spot 44 of the incident light located between a focal plane 41 and a principle plane 42.
Figure 9:
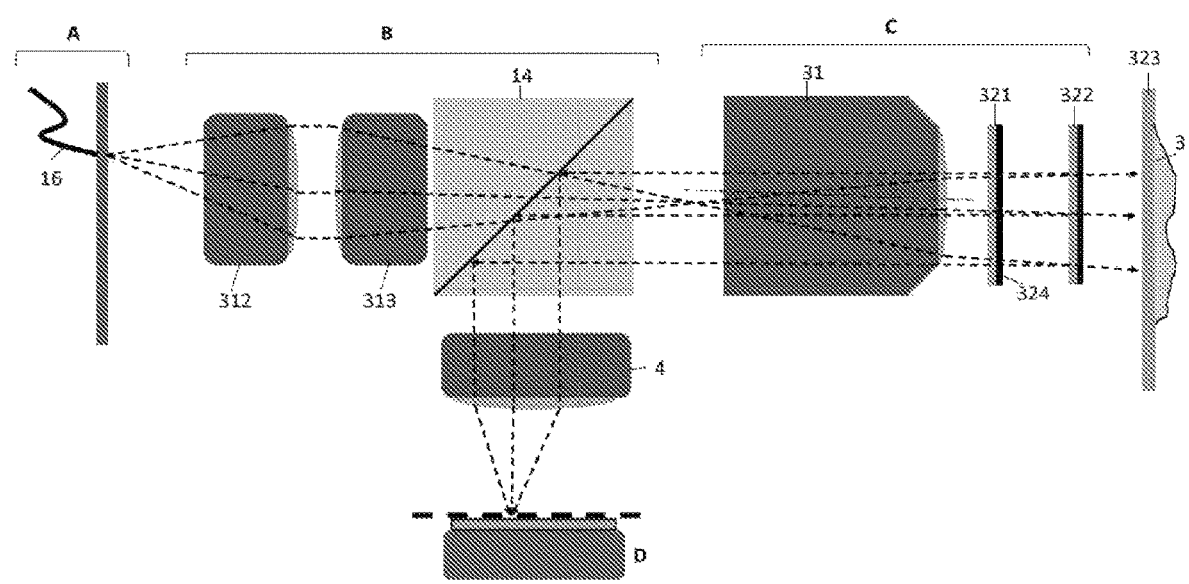
FIG. 9 further illustrates how an exemplary device/system is configured to make the stray light be focused on the edge and outside imaging range of the 2D camera D

For example, as shown in FIG. 8, the interference objective module comprising an objective 31, and an interference means (comprising a first glass plate 321 with a reflectance reference mirror 324, a second glass plate 322 and a third glass plate 323 next to a sample 3) wherein the objective 31 is configured to make the focal spot 44 of the incident light located between a focal plane 41 and a principle plane 42. Such arrangement allows the focal spot 44 of the incident light be offset from the optical axis 111 of the objective 31, which makes the stray light be focused on the edge and outside imaging range of the 2D camera D (as shown in FIG. 9). In some embodiments, the reflective reference mirror 324 is coated on the first glass plate 321 partially, for example, coated on the center of the first glass plate 321 wherein the reflective reference mirror 324 has a high reflective index made by silver, or other suitable metal used for coating.

In some embodiments, the incident light is configured to have an incident angle θ1 which is greater than 0° and less than 45° to an optical axis of the objective, Preferably, θ1 is greater than 0° and less than 20°, more preferably, greater than 0° and less than 5°, but it is not limited thereto.

In some embodiments, the focal spot is configured to have a divergence angle θ2 in a range of about 0° to 70°. The value of θ2 is depend on the field of view (FOV) and in a direct proportion to FOV. In some embodiments, an artisan can choose θ2 in a range of 0° to 20° or 5° to 15° to achieve small FOV, or choose 40° to 70° or 50° to 60° to achieve large FOV.

In some embodiments, the objective has an NA value satisfying the following formula (1):

$$NA = n \times \sin\theta, \text{ and } \theta = \theta3/(0.5\sim1.5) \tag{1}$$

NA is a numerical aperture of the objective, n is a refractive index, θ is ½ angular aperture, and θ3 is a half spreading angle form the objective.

Preferably, θ=θ3/(0.5~1.0). If the angle of θ3 is too large, it will reduce the signal correction of the sample there to reduce the sample brightness.

In some embodiments, the invention device/system comprises an illumination module configured to provide a source light (such as a line of light, or an area of light) to an optical interference module; an interference objective module comprising an objective and an interference means, which handles light from the optical interference module and process light signal generated from a sample; a two-dimensional camera to receive a backscattered interference signal from the sample; and a data processing module for analyzing light signals and providing a sample imaging, wherein device/system is configured to make the objective to accept incident light in an arrangement having a focal spot of the incident light between a focal plane and a principal plane of the objective.

As shown in FIG. 9, a light provided by an illumination module is projected to an optical interference module via an optical fiber 16. The light is collected by collimation lens 312 and then transformed to a line shaped light by cylindrical lens 313 as shown (or an area light by achromatic lens as illustrated in FIG. 7) and pass through a beam splitter 14, which will be transmitted into the interference objective module C. When the light passing through the interference objective module C to a sample 3 through the third glass plate 323, the light is absorbed, reflected or backscattered. The backscattered light signal will be collected by the interference objective module C and interferes with the reference light, which is reflected from the reflective mirror 324 and the second glass plate 322, to generate an interference signal. Then the beam splitter 14 reflects the signal to the projection lens 4 making the stray light be focused on the edge and outside imaging range of the 2D camera D.

In some embodiments, the reflective reference mirror has a shape of line, polygon (such as a square), circle spot, or other shape suitable for the device or system.

For example, as shown in FIG. 10 (10A to 10C), the reflective reference mirror 324 can have a shape of line (10A), polygon (a square, 10B), or circle spot (10C). In some embodiments, the size of the refractive reference mirror can be in a range of less than 1500 µm², preferably less than 1000 µm², preferably less than 500 µm², and preferably less than 300 µm², and a skilled person in the art would readily adjust the size as suitably needed. By coating the reflective reference mirror on the first glass plate partially, the utilization of the light will be effectively improved.

In some embodiments provide a method for imaging a sample comprising making an objective in the invention interference objective module which handles light from the optical interference module and process light signal generated from said sample to accept incident light in an arrangement having a focal spot of the incident light between a focal plane and a principal plane of the objective from an illumination module, and processing an interference signal generated said interference module into an image by a data processing module. In some embodiments, the interference objective module is any invention interference objective module disclosed herein.

The invention device/system is useful to imaging a sample in a cross-sectional as well as an en-face direction. It is particular useful in assisting in providing information of the sample surface and sub-surface such as a skin or cornea condition. The invention device/system uses a two-dimensional camera with a line-light backscattering to acquire high noise to signal ratio cross-sectional images, effectively improving the image quality and reach the resolution of 1 µm level. Also such design allows increasing the image scanning speed to 150 µm/sec or more. The use of an imaging guiding module allows the user efficiently to pinpoint the area of interest.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What claimed is:

1. A device comprising:
an illumination module configured to provide a source light to an optical interference module, which converts the source light to a line of light; an interference objective module, which handles light from the optical interference module and processes light signal generated from a sample; a two-dimensional camera configured to receive a backscattered interference signal from the sample, and a data processing module which processes the interference signal into an image, wherein the interference objective module comprises an objective and an interference means configured to process the line of light to the sample and receive a backscattered signal therefrom to generate an interference signal, wherein the line light has an aspect ratio of 3 to 100.

2. The device of claim 1, wherein the illumination source module comprises an amplified spontaneous emission light source, a superluminescent diode, a light emitting diode (LED), a broadband supercontinuum light source, a mode-locked laser, a tunable laser, a Fourier-domain Mode-locking light source, an optical parametric oscillator (OPO), a halogen lamp, a $Ce^{3+}$:YAG crystal fiber, a $Ti^{3+}$:$Al_2O_3$ crystal fiber, or a $Cr^{4+}$:YAG crystal fiber.

3. The device of claim 1, wherein the optical interference module is configured to generate a line light projected by a light source in the illumination module.

4. The device of claim 1, wherein the optical interference module comprises an anamorphic lens or a fiber bundle line array to covert the light from the light source into a line light.

5. The device of claim 1, the line light has an aspect ratio of 5 to 20.

6. The device of claim 1, wherein the interference objective module is a Mirau-type interference objective module, a Michelson-type interference module, or a Mach-Zehnder interference objective module.

7. The device of claim 1, wherein the objective is an immersed objective having the immersed solution with a refractive index in a range of about 1.2 to about 1.8.

8. The device of claim 1, wherein the device further comprises an imaging guiding module comprising a camera lens and a two-dimensional camera used for imaging guiding.

9. The device of claim 8, wherein the imaging guiding module and the interference objective module share the same optical channel or path that provides overlapped field of views.

10. The device of claim 9, wherein said interference objective module further incorporates a light source to project light onto the sample.

11. The device of claim 1, wherein the interference means comprises a first glass plate coated with a reflective mirror, a second glass plate, and a third glass plate wherein the reflective mirror is coated to generate a reference arm and produce interference with the returned scattered light by the sample.

12. The device of claim 11, wherein the reflective mirror is configured to have a shape parallel the line of light.

13. The device of claim 12, wherein the reflective mirror on the first glass plate has a shape of thin line with aspect ratio of about 1 to 5000, 4 to 1000, 8 to 250, or 10 to 100.

14. The device of claim 11, wherein the first glass plate further comprises a black spot at a position corresponding to the reflective mirror on the opposite side of the first glass plate.

15. The device of claim 14 wherein the black spot is absorptive to block the stray light.

16. The device of claim 15, wherein the position of the second plate is set to a position so that the highly reflective region is on the focal plane of the objective lens.

17. The device of claim 16, wherein the second glass plate has a reflective ratio of about 5% to 30%, or 10% to 20%.

18. The device of claim 1, wherein the optical interference module further comprises a switch configured to toggle the light between the line of light and an area of light.

19. The device of claim 18, wherein the switch toggles a cylindrical lens and an achromatic lens.

20. A device comprising:
an illumination module configured to provide a source light to an optical interference module; an interference objective module which handles light from the optical interference module and processes light signal generated from a sample; a two-dimensional camera to receive a backscattered interference signal from the sample; and a data processing module for analyzing light signals and providing a sample imaging, wherein device is configured to make the objective to accept incident light in an arrangement having a focal spot of the incident light between a focal plane and a principal plane of the objective, wherein the focal spot of the incident light is offset from the optical axis of the objective, which makes the stray light focus on the edge and outside an imaging range of the two-dimensional camera.

21. The device of claim 20, wherein the interference objective module comprises an objective and an interference means configured to process the line of light to the sample and receive a backscattered signal therefrom to generate an interference signal.

22. The device of claim 21, wherein the interference objective module is a Mirau-type interference objective module, a Michelson-type interference module, or a Mach-Zehnder interference objective module.

23. The device of claim 21, wherein the objective is an immersed objective having the immersed solution with a refractive index in a range of about 1.2 to about 1.8.

24. The device of claim 21, wherein the interference means comprises a first glass plate with a reflectance reference mirror, a second glass plate and a third glass plate next to a sample wherein the objective is configured to make the focal spot of an incident light located between a focal plane and a principal plane.

25. The device of claim 20, wherein the device further comprises an imaging guiding module comprising a camera lens and a two-dimensional camera used for imaging guiding.

26. The device of claim 25, wherein the imaging guiding module and the interference objective module share the same optical channel or path that provides overlapped field of views.

27. The device of claim 20, wherein the optical interference module is configured to generate a line light projected by a light source in the illumination module.

28. The device of claim 27, wherein the optical interference module comprises an anamorphic lens or a fiber bundle line array to covert the light from the light source into a line light.

29. A method for imaging a sample by a device of claim 20 comprising providing a source light to the optical interference module from the illumination module; handling light from the optical interference module by the interference objective module and processing a light signal generated from said sample to accept incident light in an arrangement having a focal spot of the incident light between a focal plane and a principal plane of the objective from the illumination module, and processing an interference signal from said interference objective module into an image by the data processing module.

* * * * *